(12) United States Patent
Bjorck et al.

(10) Patent No.: US 7,335,355 B2
(45) Date of Patent: Feb. 26, 2008

(54) ANTIMICROBIAL AGENT

(75) Inventors: Lars Bjorck, Lund (SE); Inga-Maria Frick, Staffanstorp (SE); Artur Schmidtchen, Lund (SE)

(73) Assignee: Hansa Medical AB, Lund (SE)

( * ) Notice: Subject to any disclaimer, the term of this patent is extended or adjusted under 35 U.S.C. 154(b) by 560 days.

(21) Appl. No.: 10/333,319

(22) PCT Filed: Jul. 17, 2001

(86) PCT No.: PCT/EP01/08208

§ 371 (c)(1),
(2), (4) Date: May 28, 2003

(87) PCT Pub. No.: WO02/06821

PCT Pub. Date: Jan. 24, 2002

(65) Prior Publication Data

US 2004/0028672 A1  Feb. 12, 2004

(30) Foreign Application Priority Data

Jul. 17, 2000  (EP) .................................. 00306074

(51) Int. Cl.
G01N 33/53 (2006.01)
G01N 33/567 (2006.01)
G01N 33/554 (2006.01)
G01N 33/569 (2006.01)
C08B 37/00 (2006.01)
A61K 38/47 (2006.01)

(52) U.S. Cl. .................. 424/94.61; 435/7.2; 435/7.32; 536/55.1

(58) Field of Classification Search ............. 424/94.61; 435/7.2, 7.32; 536/55.1
See application file for complete search history.

(56) References Cited

U.S. PATENT DOCUMENTS 5,968,525 A  10/1999  Fitzgerald et al.

FOREIGN PATENT DOCUMENTS

| EP | 0 089 939 | 9/1983 |
|---|---|---|
| EP | 0 356 060 | 2/1990 |
| WO | WO 94/03184 | 2/1994 |

OTHER PUBLICATIONS

Schmidtchen, A. et al. 2001. Dematan Sulphate is Released by Proteinases of Common Pathogenic Bacteria and Inactgivates Antibacterial a- defensin. Molecualr Microbiology, vol. 39, No. 3, pp. 708-713.*
Artur Schmidtchen et al., "Dermatan sulphate is released by proteinases of common pathogenic bacteria and inactivates antibacterial/a-defensin", *Molecular Microbiology*, 2001, pp. 708-713, vol. 39 No. 3.

Robert I. Lehrer et al., "Antimicrobial peptides in mammalian and insect host defence" Current Opinion in immunology, Current Biology LTD, XX, 1999, pp. 23-27, vol. 11, No. 1.
Efrat Kessler et al., "Pseudomonas protease. Purification, partial characterization, and its effect on collagen, proteoglycan, and rabbit corneas," *Invest. Ophthalmol, Visual Set*, 1977, pp. 488-497, vol. 16 No. 8.
Stuart I. Brown et al., "The cornea-destroying enzyme of *Pseudomonas aeruginosa*" *Invest Ophthalmology*, 1974, pp. 174-180, vol. 13, No. 6.
A. Aspedon et al., "Involvement of a Protease in Antimicrobial Peptide Resistance in *Pseudomonas aeruginosa*" XP-001064655, ASM General Meeting Session 204A/Abstract A-65, Jun. 2, 1999.
Philip Adams et al., "Defining protease specificity with proteomics: A protease with a dibasic amino acid recognition motif is regulated by a two-component signal transduction system in Salmonella", *Electrophoresis*, 1999, pp. 2241-2247, vol. 20.
Steffen Nock et al., "Reversible, site-specific immobilization of polyarginine-tagged fusion proteins and mica surfaces", *FEBS Letters*, 1997, pp. 233-238, vol. 414.
Park et al., "Exploitation of syndecan-1 shedding by *Pseudomonas aeruginosa* enchance virulence" Nature, vol. 411, pp. 98-102 (2001).
Park et al., "Syndecan-1 Shedding Is Enhanced by LasA, a Secreted Virulence Factor of *Pseudomonas aeruginosa*" The Journal of Biological Chemistry, vol. 275, No. 5, pp. 3057-3064 (2000).
O'Brien et al., Histatin 5 is a Substrate and Not an Inhibitor of the Arg- and Lys-Specific Proteinases of *Porphyromonas gingivialis* Biochemical and Biophysical Research Communications, vol. 250, pp. 474-478 (1998).

\* cited by examiner

*Primary Examiner*—Jon Weber
*Assistant Examiner*—Kailash C Srivastava
(74) *Attorney, Agent, or Firm*—Kalow & Springut LLP

(57) ABSTRACT

A method of identifying an agent that enhances the anti-microbial activity of cationic anti-microbial peptides by blocking the inhibitory effects of the proteinase/glycosaminoglycan pathway, which method comprises: (i) providing, as a first component, a cationic anti-microbial peptide; (ii) providing, as a second component, bacteria; (iii) providing, as a third component, part of all of the components of a proteinase/glycosaminoglycan pathway such that the third component reduces the antimicrobial effect of the first component, for example, a glycosaminoglycan or bacteria or bacteria and a proteoglycan or a bacterial proteinase or a bacterial proteinase and a proteoglycan; (iv) contacting the first, second and third components with a test agent under conditions that would permit the killing of the bacteria by the antimicrobial agent in the absence of the third component, and that would permit the inhibition of the anti-microbial activity of the first component by the third component in the absence of the test agent; (v) monitoring the survival of the bacterial culture thereby determining whether the test agent is capable of enhancing anti-microbial activity wherein a test agent capable of enhancing anti-microbial activity promotes killing of the bacterial culture. Agents identified by such a method are useful in the therapy of acute and chronic infections, particularly in the treatment of ulcers and in the promotion of wound healing.

7 Claims, 8 Drawing Sheets

```
           6    5    4    3    2    1
           ↓    ↓    ↓    ↓    ↓    ↓
LLGDFFRKSKEKIGKEFKRIVQRIKDFLRNLVPRTES
          _____
```

ANTIMICROBIAL AGENT

The present application is a 35 U.S.C. § 371 national stage application of PCT/EP01/08208, filed Jul. 17, 2001, which in turn claims priority to EP 00306074.6, filed Jul. 17, 2000.

FIELD OF THE INVENTION

The present invention relates to agents for use in the treatment of chronic and acute microbial infections. The invention also relates to methods for identifying agents that are useful in therapy, particularly in the treatment of chronic and acute microbial infections.

BACKGROUND OF THE INVENTION

During infection, one fundamental host defence mechanism depends on leukocyte-mediated killing of microbes. Recently, a group of cationic anti-microbial peptides, which are capable of killing various Gram-negative as well as Gram-positive bacteria by membrane disruption, have been implicated as important components of innate host defence systems in a multitude of organisms. These peptides are found in neutrophils and in epithelial cells located at biological boundaries susceptible to infection.

Pathogens appear to be able to overcome this first line of host defence, giving rise to a spectrum of clinically important conditions of an acute as well as a chronic nature. During infections bacteria utilize a combination of various strategies to overcome host defence mechanisms. Bacteria release various proteinases which modulate host specific pathways involving kallikreins, plasminogen, complement, cytokines, antibodies and antiproteinases during acute infection. Production of exotoxins and cell cycle modulating proteins by bacteria has also been reported and illustrates further the variety of pathways aimed at compromising host defence.

Bacteria such as *Streptococcus pyogenes* readily give rise to wound infections and erysipelas. *Pseudomonas aeruginosa, Enterococcus faecalis* and *Proteus mirabilis* are well known to persist in chronic wounds. These bacteria all propagate and multiply in connective tissues rich in proteoglycans (PG).

SUMMARY OF THE INVENTION

The present inventors have shown that extracellular proteinases secreted by bacteria release glycosaminoglycans, for example, by degrading proteoglycans such as those, for example, found in connective tissue. The glycosaminoglyceans may then bind to cationic anti-microbial peptides secreted by neutrophils and epithelial cells and prevent these anti-microbial peptides from killing the bacteria. In particular the present inventors have shown that dermatan sulfate-containing proteoglycans, such as decorin, are degraded by bacterial proteinases from *Pseudomonas aeruginosa, Enterococcus faecalis, Streptococcus pyogenes* and *Proteus mirabilis* to produce dermatan sulfate. They have shown that dermatan sulfate binds to neutrophil-derived α-defensin and LL-37 and that this binding completely neutralises the anti-microbial activity of α-defensin and LL-37. During infection, release of glycosaminoglycans, for example release of dermatan-sulfate by proteoglycan degradation may therefore represent an important and previously unknown bacterial defence mechanism, which could serve as a target for novel antibacterial strategies.

Accordingly, the invention provides an agent which blocks the inhibitory effects of the proteinase/glycosaminoglycan pathway for use in enhancing the antimicrobial activity of a cationic anti-microbial peptide.

The invention also provides a method of identifying an agent that enhances the anti-microbial activity of cationic anti-microbial peptides by blocking the inhibitory effects of the proteinase/glycosaminoglycan pathway, which method comprises:

(i) providing, as a first component, a cationic anti-microbial peptide;
(ii) providing, as a second component, bacteria;
(iii) providing, as a third component, part or all of the components of a proteinase/glycosaminoglycan pathway such that the third component reduces the antimicrobial effect of the first component, for example, a glycosaminoglycan or bacteria or bacteria and a proteoglycan or a bacterial proteinase or a bacterial proteinase and a proteoglycan;
(iv) contacting the first, second and third components with a test agent under conditions that would permit the killing of the bacteria by the antimicrobial agent in the absence of the third component, and that would permit the inhibition of the anti-microbial activity of the first component by the third component in the absence of the test agent;
(v) monitoring the survival of the bacteria thereby determining whether the test agent is capable of enhancing anti-microbial activity, wherein a test agent capable of enhancing anti-microbial activity promotes killing of the bacteria.

It will be appreciated that the proteinase/glycosaminoglycan pathway leading to inhibition of the cationic anti-microbial peptide may be inhibited at more than one stage and that the inhibitory action of a test agent may be monitored at each stage without the need to monitor the resultant effect on bacteria. In particular, a test agent may inhibit the interaction between the glycosaminoglycan and the cationic anti-microbial peptide, the release of glycosaminoglycan, for example the bacterial proteinase activated release of glycosaminoglycan from proteoglycan or the direct degradation of the cationic anti-microbial peptide by the bacterial proteinase. Accordingly, an agent that enhances the anti-microbial activity of cationic antimicrobial peptides by blocking the inhibitory effects of the proteinase/glycosaminoglycan pathway may be identified by any one of the following methods provided by the invention:

a method of identifying an agent which is capable of inhibiting the interaction between a glycosaminoglycan and a cationic anti-microbial peptide, which method comprises:

(i) providing, as a first component, a glycosaminoglycan;
(ii) providing, as a second component, a cationic anti-microbial peptide;
(iii) contacting the first and second components with a test agent under conditions that would permit the first and second components to interact in the absence of the test agent; and
(iv) monitoring any interaction between the first and second components thereby determining whether the test agent is capable of disrupting the interaction between the first and second components;

a method of identifying an agent which is capable of blocking the glycosaminoglycan-mediated inhibition of a cationic anti-microbial peptide, which method comprises:

(i) providing, as a first component, a glycosaminoglycan;

(ii) providing, as a second component, a cationic antimicrobial peptide;
(iii) providing, as a third component, bacteria;
(iv) contacting the first, second and third components with a test agent under conditions that would permit killing of the bacteria by the second component in the absence of the first component and that would permit inhibition by the first component of the killing of the bacteria by the second component in the absence of the test agent; and
(v) monitoring survival of the bacteria thereby determining whether the test agent is capable of preventing glycosaminoglycan-mediated inhibition of the cationic anti-microbial peptide;

a method of identifying an agent which is capable of inhibiting the degradation of a proteoglycan by a bacterial proteinase, which method comprises:
(i) providing, as a first component, a bacterial proteinase;
(ii) providing, as a second component, a proteoglycan;
(iii) contacting the first and second components with a test agent under conditions that would permit degradation of the second component by the first component in the absence of the test agent; and
(iv) monitoring any degradation of the second component thereby determining whether the test agent is capable of inhibiting the degradation of the proteoglycan by the proteinase;

a method of identifying an agent which is capable of inhibiting the degradation of a cationic anti-microbial peptide by a bacterial proteinase, which method comprises:
(i) providing, as a first component, a bacterial proteinase;
(ii) providing, as a second component, a cationic antimicrobial peptide;
(iii) contacting the first and second components with a test agent under conditions that would permit degradation of the second component by the first component in the absence of the test agent;
(iv) monitoring any degradation of the second component thereby determining whether the test agent is capable of inhibiting the degradation of the cationic anti-microbial peptide by the proteinase.

The invention also provides:
a kit suitable for use in identifying an agent which is capable of inhibiting the interaction between a glycosaminoglycan and a cationic anti-microbial peptide, which kit comprises:
(a) a glycosaminoglycan; and
(b) a cationic anti-microbial peptide;
a kit suitable for use in identifying an agent which is capable of inhibiting the degradation of a proteoglycan by a bacterial proteinase, which kit comprises:
(a) a proteoglycan; and
(b) a bacterial proteinase;
an agent identified by a method of the invention;
a pharmaceutical composition comprising an agent of the invention;
an agent or a pharmaceutical composition of the invention for use in a method of treatment of the human or animal body by therapy;
a product comprising an agent of the invention and a cationic antimicrobial peptide for simultaneous or sequential use in a method of treatment of the human or animal body by therapy;
a product comprising an inhibitor of a bacterial defence mechanism and a cationic anti-microbial peptide for simultaneous or sequential use in a method of treatment of the human or animal body by therapy, wherein the said defence mechanism comprises the degradation of a proteoglycan by a bacterial proteinase to release a glycosaminoglycan which is capable of binding to a cationic anti-microbial peptide thus inhibiting the anti-microbial activity of the said peptide;
use of an agent, a pharmaceutical composition or a product of the invention in the manufacture of a medicament for use in a method of treating a chronic or acute bacterial infection.

BRIEF DESCRIPTION OF THE FIGURES

FIG. 1 illustrates the blocking of the bactericidal activity of α-defensin by dermatan sulfate (DS).

*lis* were incubated with an amount of LL-37 that corresponded to 0.1 µg intact peptide at the start of the degradation. The peptide was incubated with the bacteria for 2 h at 37° C., in 10 mM Tris-HCl pH 7.5, 5 mM glucose. Colony forming units were determined (indicated to the left).

Figure 6:
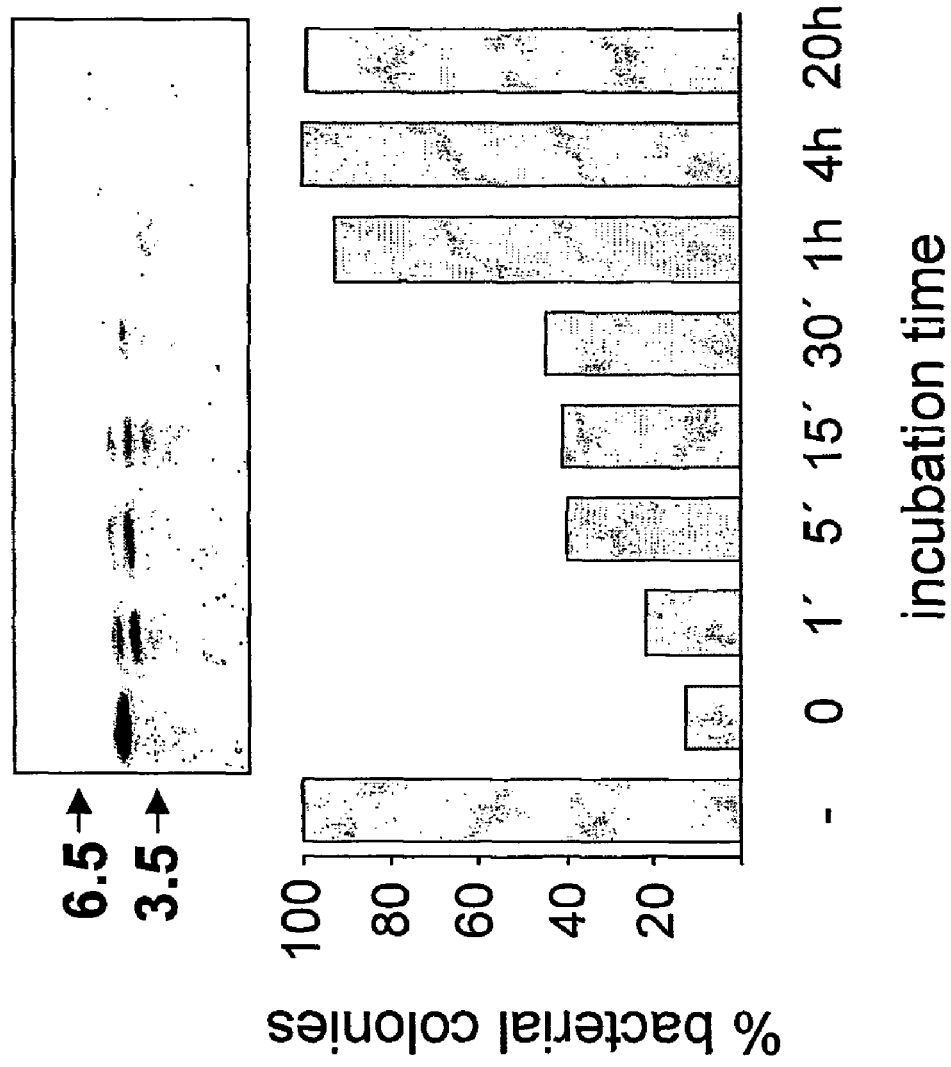
FIG. 6 shows the results of experiments which demonstrate that *Pseudomonas aeruginosa* elastase degrades and inactivates LL-37. LL-37 (10 µg) was incubated with *P. aeruginosa* elastase (30 mU) in 50 µl 10 mM Tris, pH 7.5 for various periods of time (as indicated on the x-axis). Equal aliquots of the incubations were then analysed on SDS-PAGE (16.5% Tris-Tricine gel; upper figure) or assayed for bactericidal activity (lower figure). A volume corresponding to 2 µg LL-37 was loaded on the gels. Molecular weight markers are indicated to the left (upper figure). For the bactericidal assays (lower figure), $2 \times 10^6$ cfus/ml of *E. faeca-*
Figures 7, 8:
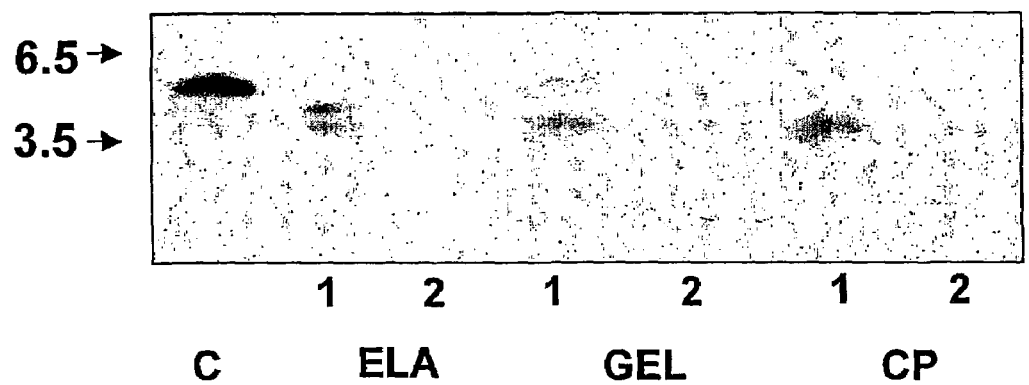

FIG. 7 shows the characterisation of LL-37 fragments. LL-37 (10 µg) was incubated with *P. aeruginosa* elastase (30 mU) in 50 µl 10 mM Tris, pH 7.5 for 1, 5, 15, 30 minutes or 1 hour. The resulting degradation products (see FIG. 6) were analysed by liquid chromatography mass spectrometry (LC-MS) followed by Time of flight (TOF) MS-MS. Major peptide fragments were detected and further analysed. The cleavage points are indicated and the proposed antibacterial region of LL-37 is underlined.

FIG. 8 shows the degradation of LL-37 by bacterial proteinases. LL-37 (1 µg) was incubated with *P. aeruginosa* elastase (ELA) for 5 minutes (1) or 1 hour (2), *E. faecalis* gelatinase containing medium (GEL), or *S. pyogenes* cysteine proteinase (CP), for 1 hour (1) or 6 hours (2), respectively. The proteinase activity added (as determined by an azocasein assay) corresponded to 6 mU (*P. aeruginosa* elastase) and 3 mU (for the other proteinases) per 10 µl reaction. The material was analysed by SDS-PAGE on 16.5% Tris-Tricine gels. Molecular weight markers are indicated to the left.

Figure 9:
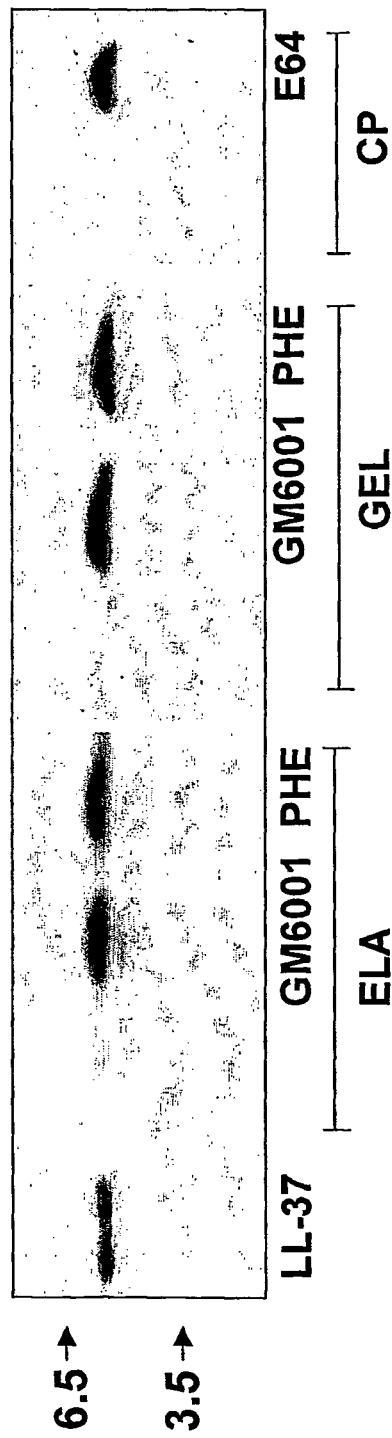

FIG. 9 shows the inhibition of LL-37 degradation by proteinase inhibitors. LL-37 (1 µg) was incubated with *P. aeruginosa* elastase (ELA, 12 mU), *E. faecalis* gelatinase (GEL, 6 mU) or *S. pyogenes* cysteine proteinase (CP, 6 mU) for 1 hour in the absence or presence of inhibitors. GM6001; 100 µM GM6001, PHE; 2 mM 1, 10-phenantroline, E64; 10 µM E64. The material was analysed by SDS-PAGE (16.5% Tris-Tricine gels). Molecular weight markers (kDa) are indicated to the left.

Figure 10:
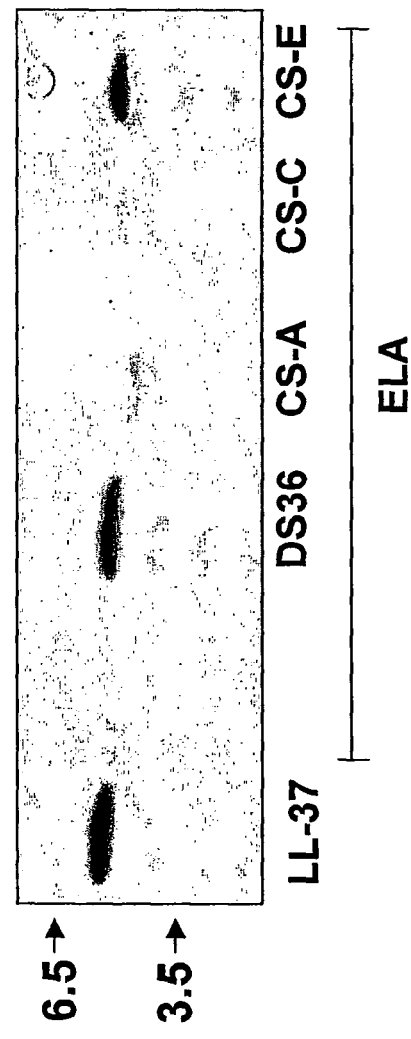

FIG. 10 shows that the degradation of LL-37 is inhibited by sulphated glycosaminoglycans. LL-37 (1 µg) was incubated with *P. aeruginosa* elastase (12 mU) in a total of volume of 15 µl (10 mM Tris-buffer) for 1 hour in the absence (ELA) or presence of the indicated glycosaminoglycans. DS36, dermatan sulphate 36 (also denoted CS-B), CS-A; chondroitin sulphate A, CS-C, chondroitin sulphate C, CS-E; chondroitin sulphate E. The material was analysed by SDS-PAGE on 16.5% Tris-Tricine gels. Molecular weight markers (kDa) are indicated to the left.

Figure 11:
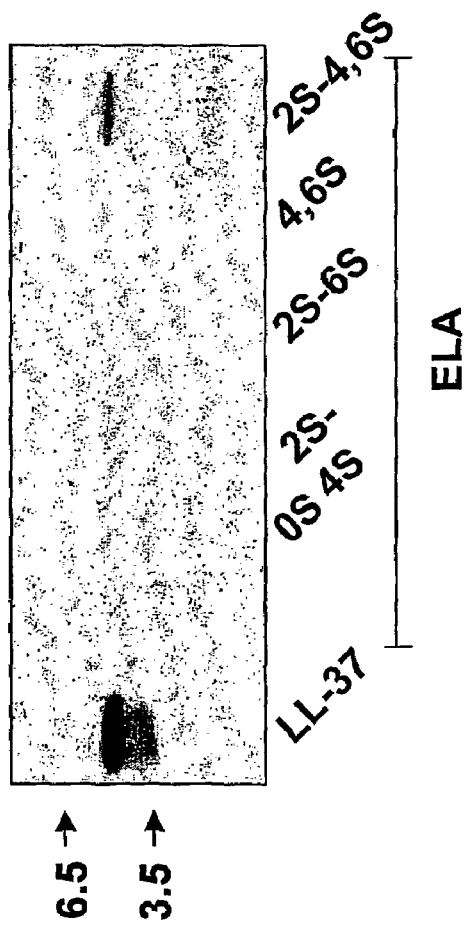

FIG. 11 shows that the degradation of LL-37 is inhibited by sulphated disaccharides. LL-37 (1 µg) was incubated with *P. aeruginosa* elastase (12 mU) in a total of volume of 15 µl (10 mM Tris-buffer) for 1 hour in the absence or presence of sulfated disaccharides, ELA; *P. aeruginosa* elastase, 0S, UA-GalNAc; 2S4S; UA(2S)-GalNAc(4S), 2S-6S; UA(2S)-GalNAc(6S), 4, 6diS; UA-GalNAc(4,6S), 2S-4,6diS; UA(2S)-GalNAc(4,6S). The material was analysed by SDS-PAGE on 16.5% Tris-Tricine gels. Molecular weight markers (kDa) are indicated to the left.

Figure 12:
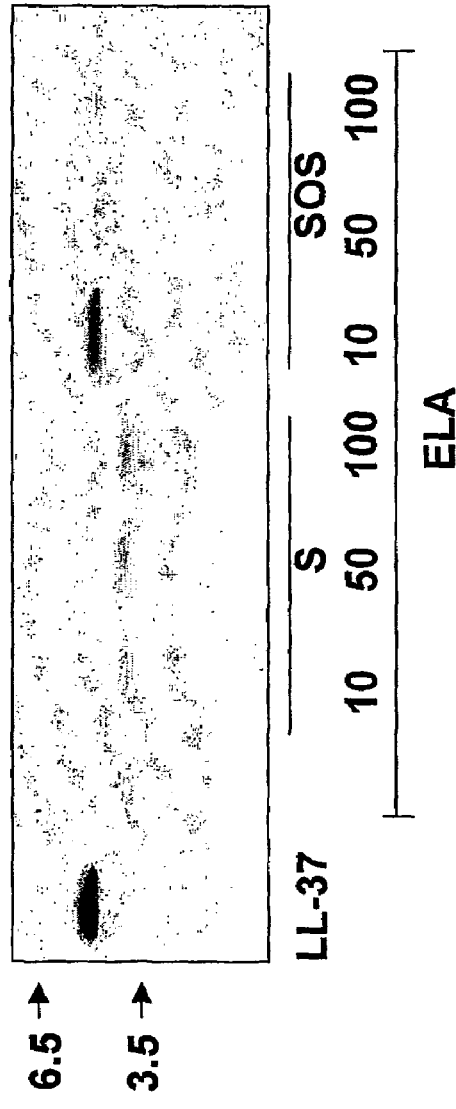

FIG. 12. shows that the degradation of LL-37 is inhibited by sucroseoctasulphate. LL-37 (1 µg) was incubated with *P. aeruginosa* elastase (12 mU; ELA) in a total of volume of 15 µl (10 mM Tris-buffer) for 1 hour in the absence or presence of sucrose (S) or sucroseoctasulphate (SOS) of the indicated amounts (in nanomoles). The material was analysed by SDS-PAGE on 16.5% Tris-Tricine gels. Molecular weight markers (kDa) are indicated to the left.

BRIEF DESCRIPTION OF THE SEQUENCE LISTING

SEQ ID NO: 1 is the amino acid sequence of the cationic antimicrobial peptide LL-37.
SED ID NO: 2 is the amino acid sequence of the cationic antimicrobial peptide α-defensin.

DETAILED DESCRIPTION OF THE INVENTION

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The present invention provides methods for identifying an agent that enhances the action of a cationic anti-microbial peptide by interfering with a bacterial defence mechanism. The bacterial defence mechanism comprises the release of a glycosaminoglycan and the binding of the released glycosaminoglycan to cationic anti-microbial peptide. Binding of the glycosaminoglycan to the cationic anti-microbial peptide inhibits anti-microbial activity of the peptide (herein referred to as proteinase/glycosaminoglycan pathway). The glycosaminoglycan may be released by the degradation of a proteoglycan. Preferably the proteoglycan is degraded by a bacterial proteinase. Other mechanisms of glycosaminoglycan release include enhanced shedding of proteoglycans mediated by endogenous metalloproteinases, increased production of proteoglycans and displacement of proteoglyeans from binding sites in the connective tissue. For example, bacterial proteinase may directly effect activation of endogenous matrix metalloproteinases. Interference may, for example, be blocking degradation of proteoglycan, for example by inhibiting proteinase binding or activity, or by blocking binding of glycosaminoglycan to the cationic anti-microbial peptide.

Cationic antimicrobial peptides are well known in the art. See, for example, Lehrer, R. I, and Ganz, T. (1999) Antimicrobial peptides in mammalian and insect host defence *Curr Opin Immunol* 11; 23-27.

The cationic anti-microbial peptide is typically an antibacterial peptide that is capable of disrupting the bacterial membrane, thus killing the bacteria. The cationic anti-microbial peptide may be added exogenously. Preferably the cationic anti-microbial peptide is produced by a leukocyte and/or by an epithelial cell at a site of infection. Preferably the leukocyte is a neutrophil. The cationic anti-microbial peptide is preferably a defensin or a cathelicidin. More preferably the cationic antimicrobial peptide is α-defensin (SEQ ID NO: 2) or LL-37 (SEQ ID NO: 1). The cationic anti-microbial peptide may comprise a variant or fragment of SED ID NO: 1 or SEQ ID NO: 2 which variant or fragment exhibits antimicrobial, preferably antibacterial, activity. For example, the cationic antimicrobial peptide may be a fragment of SEQ ID NO: 1 comprising the seqeunce underlined in FIG. 7.

The cationic anti-microbial peptide provided for use in a method of the invention may be from any suitable source. For example, the cationic anti-microbial peptide may be recombinant peptide, the cationic anti-microbial peptide may be purified from a leukocyte or epithelial cell or the cationic anti-microbial peptide may be present in growth medium extracted from leukocytes, epithelial cells or cells transfected with recombinant peptide grown in culture. The peptide may comprise a natural sequence or may comprise an artificially mutated sequence provided that the mutation does not affect the ability of the peptide to disrupt bacterial membranes or to interact with a glycosaminoglycan.

A typical assay for determining whether a peptide exhibits anti-microbial activity comprises incubating bacteria, such as *Pseudomonas aeruginosa, Enterococcus faecalis, Streptococcus pyogenes, Proteus mirabilis* or *E. coli*, with the peptide and monitoring the survival of the bacteria. Typically the anti-microbial peptide will effectively kill the bacteria at concentrations of from 4 µg/ml, for example at concentrations of 4 µg/ml, 5 µg/ml, 10 µg/ml, 20 µg/ml, 40 µg/ml, 100 µg/ml or 500 µg/ml.

Survival of the bacteria may be monitored by any suitable method. Typically the number of colony forming units may be determined. Survival of bacteria may also be monitored indirectly by assessing the effect of the bacteria on a host animal or host cell.

The bacteria may be of any suitable strain. The bacteria may be gram negative or gram positive. Preferably the bacterial stain is one found at a site of infection in the human or in an animal. Preferably the site of infection is a barrier to pathogen entry into the human or animal such as the skin or a mucosal membrane. Preferably the bacteria are *Pseudomonas aeruginosa, Enterococcus faecalis, Streptococcus pyogenes* or *Proteus mirabilis*.

Any suitable bacterial preparation may be used in a method of the invention or in an assay described herein. For example, the bacteria may be grown to mid-log phase in TH-medium or in C-medium. The bacteria may then be washed and diluted, for example in 10 mM Tris-HCl, pH 7.5 containing 5 mM glucose. Typically from 5 µl to 500 µL bacteria, preferably from 101 µl to 100 µl bacteria (2×106 cfu/ml) are used per assay. Incubations of bacteria with the anti-microbial peptide, the anti-microbial peptide and glycosaminoglycan, the anti-microbial peptide and test substance or anti-microbial peptide, glycosaminoglycan and test substance are typically carried out at 37° C. for from 30 minutes to 6 hours, preferably from 2 hours to 4 hours. Anti-microbial activity may be quantified by any suitable method, for example, by making serial dilutions of the incubation mixture, plating the dilutions on agar (such as TH-agar), incubating at 37° C., preferably overnight, and determining the number of colony forming units (CFU) produced.

A glycosaminoglycan suitable for use in a method of the invention is capable of interacting with the cationic anti-microbial peptide in such a way that the anti-microbial function of the peptide is inhibited. The glycosamioglycan is typically an endogenous glycosaminoglycan. The glycosaminoglycan is preferably heparan sulfate or heparin and is more preferably dermatan sulfate. Preferably a glycosaminoglycan suitable for use in a method of the invention exhibits a high degree of sulfation and/or iduronate content. The iduronate content is typically at least 50%, for example at least 60%, at least 70%, at least 80% or at least 90%. The degree of sulfation is typically at least 50%, for example at least 60%, at least 70%, at least 80% or at least 90%. A glycosaminoglycan for use in a method of the present invention may also comprise additional modifications, for example the iduronate may be 2-O-sulfated.

A typical assay for determining whether a glycosaminoglycan is capable of interacting with a cationic anti-microbial peptide comprises immobilising a cationic anti-microbial peptide, for example on nitrocellulose, and probing with radiolabelled glycosaminoglycan. Preferably binding of the glycosaminoglycan to the peptide may be inhibited with excess unlabelled dermatan sulfate.

A typical assay for determining whether a glycosaminoglycan peptide is capable of inhibiting anti-microbial activity of a cationic anti-microbial peptide comprises incubating a preparation or culture of bacteria, such as *Pseudomonas aeruginosa, Enterococcus faecalis, Streptococcus pyogenes* or *Proteus mirabilis*, with the glycosaminoglycan and the peptide and monitoring the killing of the bacteria. Typically the anti-microbial peptide will be added at a concentration that would effectively kill the bacteria in the absence of the glycosaminoglycan. Typically the glycosaminoglycan inhibits the peptide-mediated killing of the bacteria at a concentration of from 10 µg/ml to 1 mg/ml, more preferably from 10 µg/ml to 500 µg/ml or most preferably from 20 µg/ml to 250 µg/ml. The molar ratio of glycosaminoglycan to cationic anti-microbial peptide is typically from 0.1:1 to 1000:1, preferably from 0.5:1 to 100:1 and more preferably from 0.5:1 to 10:1. The glycosaminoglycan may only partially inhibit the anti-microbial activity of the peptide. Preferably the glycosaminoglycan inhibits anti-microbial activity by at least 2%, for example at least 6%, at least 16%, at least 30% or at least 40%. More preferably the anti-microbial activity is inhibited by the glycosaminoglycan by at least 50%, for example at least 60%, at least 70%, at least 80%, at least 90% or at least 99%.

The glycosaminoglycan may be obtained from any suitable source. Preferably the glycosaminoglycan is obtained from connective tissue such as dermis (skin) or cartilage. The glycosaminoglycan may be prepared by any suitable method, for example as described in L. Rodén, J. Baker, J. A. Cifonelli, M. B. Mathews, in *Methods in Enzymology*, V. Ginsburg, ed. (Academic Press, New York, 1973), vol. 28, pp. 73-140, L.-Å. Fransson, I. A. Nieduszynski, C. F. Phelps, J. K. Sheehan, Biochim. Biophys. Acta., 586, 179 (1979) or L.-Å. Fransson, I. Sjöberg, B. Havsmark, *Eur. J. Biochem.*, 106, 59 (1980).

Typically, a glycosaminoglycan for use in a method of the invention may be produced by the action of one or more proteinase, for example a bacterial proteinase, on one or more proteoglycan. The glycosaminoglycan may be provided indirectly by providing a suitable bacterial proteinase and a suitable proteoglycan. The proteoglycan may be an extracellular product of a fibroblast culture. Preferably the proteoglycan comprises heparin, heparan sulfate or more preferably dermatan sulfate. Preferably the proteoglycan is biglycan, syndecan, glypican or CD44. More preferably the proteoglycan is decorin or versican.

A typical assay for determining whether a proteoglycan is degraded by a bacterial proteinase comprises radiolabelling the proteoglycan with $^{35}S$, incubating the labelled proteoglycan with a bacterial proteinase, running a sample of the labelled proteoglycan taken prior to the incubation and a sample taken after the incubation on a SDS-polyacrylamide gel and determining the relative sizes and amounts of the labelled proteoglycan and degradation products. It may be necessary to include a reducing agent, such as DTT in the incubation mix, for example if the bacterial proteinase is a cysteine proteinase. The proteoglycan may be taken from any suitable source, for example it may be an extracellular product of a fibroblast culture. Preferably the proteoglycan has a molecular weight of from 80 to 500 kDa, preferably about 100 kDa or about 400 kDa. The degradation products preferably have a molecular weight of from 30 to 50 kDa, corresponding to the size of free or peptide linked glycosaminoglycan chains.

Any suitable proteinase may be used in the assays described herein. Preferably the proteinase is a bacterial proteinase. Any bacterial preparation or bacterial culture may be used as a source of a bacterial proteinase. The bacteria may be stimulated to produce proteinase by any suitable means. Growth media from cultures of bacteria may be used. Typically, bacteria are grown to stationary phase in liquid media, for example in TH-medium or in C-medium. Growth media suitable for use in a method of the invention may be obtained by pelleting the bacteria by centrifugation and filtering the supernatant, for example, through a filter of from 0.2 µm to 0.4 µm in diameter. Alternatively bacterial proteinases may be isolated from the growth medium. Any suitable method may be used to isolate a bacterial proteinase. For example, a proteinase may be prepared by ammonium sulphate precipitation, dialysis and separation on a suitable column such as a High Q anion exchange column. Alternatively a proteinase may be prepared as described in H. Herwald, M. Collin, W. Muller-Esterl, L. Björck, *J. Exp. Med.* 184, 665 (1996). Bacterial proteinases suitable for use in the invention include *Pseudomonas aeruginosa* elastase, *Pseudomonas aeruginosa* alkaline proteinase, *Enterococcus faecalis* gelatinase and *Streptococcus pyogenes* cysteine proteinase.

A method of identifying an agent that enhances cationic anti-microbial peptide activity provided by the present invention may comprise a method of identifying an agent which is capable of inhibiting the interaction between a glycosaminoglycan and a cationic anti-microbial peptide. Such a method may consist essentially of:
   (i) providing, as a first component, a glycosaminoglycan;
   (ii) providing, as a second component, a cationic anti-microbial peptide;
   (iii) contacting the first and second components with a test agent under conditions that would permit the first and second components to interact in the absence of the test agent; and
   (iv) monitoring any interaction between the first and second components thereby determining whether the test agent is capable of disrupting the interaction between the first and second components.

A glycosaminoglycan and a cationic anti-microbial peptide suitable for use in this method have been previously described herein. Any suitable conditions may be used for contacting the first and second components with the test agent. Typically, the cationic peptide may be immobilised, for example on a nitrocellulose membrane or on a polyacrylamide gel, which is preferably non-denaturing, and the immobilised peptide is incubated with the glycosaminoglycan and the test agent. The binding of glycosaminoglycan to the immobilised peptide and hence the ability of the test agent to compete for binding may be monitored by any suitable means. For example, the glycosaminoglycan may be radiolabelled, for example with $^{35}S$, and radiolabelled glycosaminoglycan bound to the immobilised peptide may be detected by any suitable means such as scintillation counting, using a phosphorimager or using X-ray film. Preferably experiments with and without the test substances are carried out under identical conditions, ideally at the same time, and the results of the experiments are compared to determine whether the test agent causes a reduction in the binding of the glycosaminoglycan to the peptide. Generally the test substances are added in excess. Preferably the test agent causes a reduction in the binding of the glycosaminoglycan to the peptide by at least 20%, at least 30%, at least 40%, at least 50%, at least 60%, at least 70%, at least 80%, at least 90%, at least 95%, at least 99% or substantially prevents the binding of the glycosaminoglycan to the peptide at a concentration of the agent of 0.1 mg ml$^{-1}$, 1 mg ml$^{-1}$, 10 mg ml$^{-1}$, 100 mg ml$^{-1}$, 500 mg ml$^{-1}$, 1 mg ml$^{-1}$, 10 mg ml$^{-1}$, 100 mg ml$^{-1}$ or 0.1 g ml$^{-1}$. Any combination of the above percentage reductions in the degree of interaction and concentrations of product may be used to define an agent of the invention, with greater disruption at lower concentrations being preferred. Preferred agents of the invention are those which show at least a 50% level of inhibition at a concentration of 1 mg ml$^{-1}$ or 0.5 mg ml$^{-1}$.

A method of identifying an agent that enhances cationic anti-microbial peptide activity provided by the present invention may comprise a method of identifying an agent which is capable of blocking the inhibitory effect of a glycosaminoglycan on the anti-microbial activity of a cationic anti-microbial peptide. Such a method may consist essentially of:
   (i) providing, as a first component, a glycosaminoglycan;
   (ii) providing, as a second component, a cationic anti-microbial peptide;
   (iii) providing, as a third component, bacteria;
   (iv) contacting the first, second and third components with a test agent under conditions that would permit killing of the bacteria by the second component in the absence of the first component and that would permit inhibition by the first component of the killing of the bacteria by the second component in the absence of the test agent; and
   (v) monitoring killing of the bacteria thereby determining whether the test agent is capable of preventing glycosaminoglycan-mediated inhibition of the cationic anti-microbial peptide.

In step (iv) the first and second components may first be contacted with a test agent and then contacted with the third component. The third component may be contacted with a mixture of the first component, second component and test agent at any suitable time after contacting the first two components with the test agent, for example from 0 to 4 hours, such as 30 seconds, 1 minute, 5 minutes, 15 minutes, 30 minutes or 1 hour.

The test agents may first be tested for any direct effect on activity of the cationic anti-microbial peptide. Preferably, only test agents which do not inhibit cationic anti-microbial peptide activity are used in a bactericidal assay.

A glycosaminoglycan, a cationic anti-microbial peptide and a bacterial preparation suitable for use in this method have been previously described herein. Any suitable conditions may be used for contacting the first, second and third components with the test agent. Typically from 5 µl to 500 µl bacteria, preferably from 10 µL to 100 µl bacteria (2×10$^6$ cfu/ml) are used per assay. The three components are typically incubated together at 37° C. for from 30 minutes to 6 hours, preferably from 2 hours to 4 hours. Monitoring the killing of bacteria may be carried out by any known method, for example, anti-microbial activity may be quantified by making serial dilutions of the incubation mixture, plating the dilutions on agar (such as TH-agar), incubating at 37° C., preferably overnight, and determining the number of colony forming units (CFU) produced. Preferably three assays one containing only the second component (anti-microbial peptide), one containing only the first and second components (glycosaminoglycan and anitimicrobial peptide) and one containing all three components, are carried out under identical conditions and preferably simultaneously. The results of the three assays may be quantified and the results may be compared to determine the effectiveness of the test agent at blocking the inhibition of anti-microbial activity by the glycosaminoglycan. Preferably the test agent reverses the blocking effect of the glycosamoinoglycan on the anti-microbial activity of the peptide by at least 20%, at least 30%, at least 40%, at least 50%, at least 60%, at least 70%, at least 80%, at least 90%, at least 95%, at least 99% or substantially prevents the inhibition of cationic anti-microbial peptide activity at a concentration of the agent of 0.1 mg ml$^{-1}$, 1 mg ml$^{-1}$, 10 mg ml$^{-1}$, 100 mg ml$^{-1}$, 500 mg ml$^{-1}$, 1 mg ml$^{-1}$, 10 mg ml$^{-1}$, 100 mg ml$^{-1}$ or 0.1 g ml$^{-1}$. Any combination of the above percentage reductions in the degree of inhibition and concentrations of product may be used to define an agent of the invention, with greater disruption at lower concentrations being preferred. Preferred agents of the invention are those which show at least a 50% level of inhibition at a concentration of 1 mg ml$^{-1}$ or 0.5 mg ml$^{-1}$.

Degradation of the second component may also be monitored indirectly by monitoring the killing of bacteria by a cationic anti-microbial peptide in the presence and absence of test agent using an assay as described previously herein.

A method of identifying an agent that enhances cationic anti-microbial peptide activity provided by the present invention may comprise a method of identifying an agent which is capable of inhibiting the release of a glycosaminoglycan, for example by blocking the degradation of a proteoglycan by a bacterial proteinase, which glycosaminoglycan is then free to interact with a cationic anti-microbial peptide. Such a method may consist essentially of:

(i) providing, as a first component, a bacterial proteinase;
(ii) providing, as a second component, a proteoglycan;
(iii) contacting the first and second components with a test agent under conditions that would permit degradation of the second component by the first component in the absence of the test agent; and
(iv) monitoring any degradation of the second component thereby determining whether the test agent is capable of inhibiting the degradation of the proteoglycan by the proteinase.

Suitable first and second components and a typical assay for determining whether a proteoglycan is degraded by a bacterial proteinase have been described previously herein. Preferably two assays, one including the test agent and one omitting the test agent, are carried out under identical conditions. The degree of inhibition of degradation by the test agent may then be determined by comparing the relative amount of degradation products and/or the relative amounts of non-degraded proteoglycan between the two assays. The relative amounts of each product may be quantified using a phosphorimager. Preferably, a test substance that inhibits the degradation of a proteoglycan by a proteinase will reduce the degradation of the proteoglycan by at least 20%, at least 30%, at least 40%, at least 50%, at least 60%, at least 70%, at least 80%, at least 90%, at least 95%, at least 99% or substantially prevent the degradation of the proteoglycan at a concentration of the agent of 0.1 mg ml$^{-1}$, 1 mg ml$^{-1}$, 10 mg ml$^{-1}$, 100 mg ml$^{-1}$, 500 mg ml$^{-1}$, 1 mg ml$^{-1}$, 10 mg ml$^{-1}$, 100 mg ml$^{-1}$ or 0.1 g ml$^{-1}$. Any combination of the above percentage reductions in the degree of interaction and concentrations of product may be used to define an agent of the invention, with greater disruption at lower concentrations being preferred. Preferred agents of the invention are those which show at least a 50% level of inhibition at a concentration of 1 mg ml$^{-1}$ or 0.5 mg ml$^{-1}$.

A method of identifying an agent that enhances cationic anti-microbial peptide activity provided by the present invention may comprise a method of identifying an agent which is capable of preventing the degradation of a cationic antimicrobial peptide by a bacterial proteinase. Such a method may consist essentially of:

(i) providing, as a first component, a bacterial proteinase;
(ii) providing, as a second component, a cationic anti-microbial peptide;
(iii) contacting the first and second components with a test agent under conditions that would permit degradation of the second component by the first component in the absence of the-test agent;
(iv) monitoring any degradation of the second component thereby determining whether the test agent is capable of inhibiting the degradation of the cationic anti-microbial peptide by the proteinase.

Suitable first and second components have been described previously herein. A typical assay for determining whether a cationic anti-microbial peptide is degraded by a bacterial proteinase may comprise radiolabelling the peptide with 35%, incubating the labelled peptide with a bacterial proteinase, running a sample of the labelled peptide taken prior to the incubation and a sample taken after the incubation on a SDS-polyacrylamide gel and determining the relative amounts of the labelled peptide and degradation products. It may be necessary to include a reducing agent such as DTT in the incubation mix, for example if the bacterial proteinase is a cysteine proteinase. Preferably two assays, one including the test agent and one omitting the test agent, are carried out under identical conditions. The degree of inhibition of degradation by the test agent may then be determined by comparing the relative amount of degradation products and/or the relative amounts of non-degraded peptide between the two assays. The relative amounts of each product may be quantified using a phosphorimager. Preferably, a test substance that inhibits the degradation of a peptide by a proteinase will reduce the degradation of the peptide by at least 20%, at least 30%, at least 40%, at least 50%, at least 60%, at least 70%, at least 80%, at least 90%, at least 95%, at least 99% or substantially prevent the degradation of the peptide at a concentration of the agent of 0.1 mg ml$^{-1}$, 1 mg ml$^{-1}$, 10 mg ml$^{-1}$, 100 mg ml$^{-1}$, 500 mg ml$^-$, 1 mg ml$^{-1}$, 10 mg ml$^{-1}$, 100 mg ml$^{-1}$ or 0.1 g ml$^{-1}$. Any combination of the above percentage reductions in the degree of interaction and concentrations of product may be used to define an agent of the invention, with greater disruption at lower concentrations being preferred. Preferred agents of the invention are those which show at least a 50% level of inhibition at a concentration of 1 mg ml$^{-1}$ or 0.5 mg ml$^{-1}$.

Other suitable methods for monitoring peptide degradation include protein staining, immunoblotting and radioiodination. Peptide degradation may also be monitored using a functional assay, for example by determining whether there is any residual antibacterial activity of the degradation products. Antibacterial activity may be determined using bactericidal assays and measuring colony forming units (cfus).

Degradation of the second component may also be monitored indirectly by monitoring the killing of bacteria by the cationic anti-microbial peptide in the presence and absence of test agent using an assay as described previously herein.

The present invention also provides a kit for identifying a test agent that enhances cationic anti-microbial peptide activity, which kit comprises:

(i) a glycosaminoglycan; and
(ii) a cationic anti-microbial peptide.

The kit may further comprise:

(iii) a bacterial sample; and/or (iv) a means for determining whether a test agent inhibits the interaction between the glycosaminoglycan and the cationic anti-microbial peptide.

The present invention also provides a kit for identifying a test agent that enhances cationic anti-microbial peptide activity, which kit comprises:
(i) a proteoglycan;
(ii) a bacterial proteinase The kit may further comprise:
(ii) a means for determining whether a test agent inhibits the degradation of the proteoglycan by the bacterial proteinase.

A kit provided by the present invention may also comprise:
(v) or (iv) instructions for carrying out an assay to determine the ability of a test agent to enhance the cationic anti-microbial peptide activity.

The term 'agent' is intended to include a single substance and a combination of two, three or more substances. For example, the term agent may refer to a single peptide, a mixture of two or more peptides or a mixture of a peptide and a defined chemical entity.

Any suitable test agent may be used in a method of the invention. Preferably the test substance is non-toxic to eukaryotic cells. Preferred test agents which can be tested in the above assays include carbohydrates, molecules comprising a carbohydrate backbone with chemical modifications such as sulfation and/or carboxylation, peptides and peptide mimetics. Particularly preferred test agents include cationic substances which may function as scavengers for released glycosaminoglycans, polyethyleneimine, protamine, polybrene, poly-L-lysine, poly-L-arginine, chitosan and polymyxin. Other suitable test agents include combinatorial libraries, defined chemical entities, oligonucleotides and natural product libraries, such as display libraries (for example phage display libraries). Furthermore, antibody products (for example, monoclonal and polyclonal antibodies, single chain antibodies, chimeric antibodies, CDR-grafted antibodies and humanised antibodies) or fragments thereof may be used. Examples of suitable test agents are shown in Table 1.

TABLE 1

| Anionic substances | Structure |
| --- | --- |
| HS3 | 4GlcA (+/−2S)-GlcNAc(+/−6S)-IdoA(+/−2S)-GlnSO3(+/−3S,+/−6S) |
| HS4 | |
| HS5 | |
| HS6 | |
| disaccharides from HS | UA(2S)-G1cN(6S) |
| | UA(2S)-GlcN(6S) |
| | UA(2S)-GlcN |
| | UA(2S)-GlcNS(6S) |
| | UA(2S)-GlcNS |
| | UA-GlcN(6S) |
| | UA-GlcN |
| | UA-GlcNS(6S) |
| CS-6 | GlcA-GalNAc(6S) polymer |
| CS-4 | GlcA-GalNAc(4S) polymer |
| DS36 | IdoA(+/−2S)-GalNAc(4S) / GlcA-GalNAc(6S) polymer |
| DS13 | |
| disaccharides from CS/DS | UA-GalNAc |
| | UA-GalNAc(4S) |
| | UA-GalNAc(6S) |
| | UA(2S)-GalNAc |
| | UA(2S)-GalNAc(4S) |
| | UA(2S)-GalNAc(6S) |
| | UA(2S)-GalNAc(6, 4S) |
| | UA-GalNAc(6, 4S) |
| CS-D | GlcA(2S)-GalNAc(4S) polymer |
| CS-E | GlcA-GalNAc(4, 6S) polymer |
| sucroseoctasulfate | sucrose/8 sulphates |
| Carragenan | ~1 sulphate/disacch |
| | ~2 sulphate/disacch |
| | ~3 sulphate/disacch |
| Dextransulfate | |
| Dextran | |
| Heparin | |
| LMW-Heparin | |
| Cationic substances | |
| poly-L-Lysine | |
| poly-L-Arginine | |
| DEAE-dextran | |
| polybrene (hexadimetrinebromide) | |
| protamine | |
| polymyxin B | |
| polymyxin B nonapeptide | |
| polyethyleneimine | |
| chitosan | |
| Proteinase inhibitors | |
| Ilomostat (GM 6001) etc | |

A carbohydrate test agent may be a monosaccharide, a disaccharide, an oligosaccharide or a polysaccharide. For example, a polymer of chondroitin sulfate [GlcA-GalNAc]$_n$, or dermatan sulfate. Preferably the carbohydrate test agent is capable of binding to the cationic anti-microbial peptide without affecting its antimicrobial activity.

A peptide test agent may be a mimic of a cationic anti-microbial peptide. Preferably the mimic is capable of binding to a glycosaminoglycan and/or to a protesase to sequester the glycosaminoglycan and/or proteinase thus preventing the glycosaminoglycan and/or protesase from interacting with the cationic anti-microbial peptide. The mimic may mimic only the region of a cationic anti-microbial peptide that binds to the glycosaminoglycan or may also mimic a region of the peptide with anti-microbial activity. A test peptide may also comprise any other amino acid sequence. Preferably a peptide comprises an amino acid sequence that enables it to interact with the glycosaminoglycan and/or proteinase to prevent their binding to a cationic anti-microbial peptide.

Test agents may be used in an initial screen of, for example, 10 substances per reaction, and the agents of these batches which show inhibition or activation tested individually. Test agents may be used at a concentration of from 1 nM to 100 μM, preferably from 1 μM to 100 μM or from 5 μM to 50 μM, more preferably from 1 μM to 10 μM.

The invention also provides a product containing an inhibitor of a bacterial proteinase/glycosaminoglycan defence pathway and a cationic anti-microbial peptide for simultaneous or sequential use in a method of treatment of the human or animal body by therapy.

The inhibitor may be capable of blocking the interaction between a glycosaminoglycan and a cationic anti-microbial peptide, blocking the degradation of a proteoglycan by a bacterial proteinase or blocking degradation of a cationic antimicrobial peptide by a bacterial proteinase. An inhibitor capable of blocking the interaction between a glycosaminoglycan and a cationic anti-microbial peptide may bind to the glycosaminoglycan to prevent it binding to the cationic anti-microbial peptide or may bind to the cationic anti-microbial peptide such that the peptide retains its anti-microbial activity but is unable to bind to the inhibitory glycosaminoglycan.

Preferred inhibitors include carbohydrates, molecules comprising a carbohydrate backbone with chemical modifications such as sulfation and/or carboxylation, peptides and peptide mimetics. Other suitable inhibitors include combinatorial libraries, defined chemical entities, oligonucleotides and natural product libraries, such as display libraries (for example phage display libraries).

An inhibitor may be a mimic, for example a peptide, of a cationic antimicrobial peptide. Preferably the mimic is capable of binding to a glycosaminoglycan and/or to a protesase to sequester the glycosaminoglycan and/or proteinase thus preventing the glycosaminoglycan and/or protesase from interacting with the cationic anti-microbial peptide. The inhibitor may mimic only the region of a cationic anti-microbial peptide that binds to the glycosaminoglycan or may also mimic a region of the peptide with anti-microbial activity. Preferably the mimic is a peptide comprising an amino acid sequence that enables it to interact with the glycosaminoglycan and/or proteinase to prevent their binding to a cationic antimicrobial peptide.

The inhibitor is preferably a monosaccharide, a disaccharide, an oligosaccharide or a polysaccharide. More preferably the inhibitor is a cationic substance, such as polyethyleneimine, protamine, polybrene, poly-L-lysine, poly-L-arginine, chitosan or polymyxin. Preferably the inhibitor is capable of binding to the cationic anti-microbial peptide without affecting its anti-microbial activity.

The cationic anti-microbial peptide is a peptide that is capable of disrupting the bacterial membrane, thus killing the bacteria. Preferably the cationic anti-microbial peptide is produced by a leukocyte and/or by an epithelial cell at a site of infection. Preferably the leukocyte is a neutrophil. The cationic anti-microbial peptide is preferably a cationic antibacterial peptide such as a defensin or LL-37. More preferably the cationic anti-microbial peptide is α-defensin. The cationic anti-microbial peptide provided for use in a method of the invention may be from any suitable source. For example, the cationic anti-microbial peptide may be recombinant peptide, the cationic anti-microbial peptide may be purified from a leukocyte or endothelial cell or the cationic anti-microbial peptide may be present in growth medium extracted from leukocytes, epithelial cells or cells transfected with recombinant peptide grown in culture. The peptide may be produced by in vitro protein synthesis. The peptide may comprise a natural sequence or may comprise an artificially mutated sequence provided that the mutation does not affect the ability of the peptide to disrupt bacterial membranes or to interact with a glycosaminoglycan.

The invention also provides a product containing two or more inhibitors of a bacterial proteinase/glycosaminoglycan defence pathway for simultaneous or sequential use in a method of treatment of the human or animal body by therapy. In addition, the invention provides a product containing two or more agents of the invention or simultaneous or sequential use in a method of treatment of the human or animal body by therapy.

Agents identified by a method of the invention and products of the invention may be used in a method of treatment of the human or animal body by therapy. In particular such agents, and products, may be used in the treatment of acute or chronic bacterial infections, in the treatment of ulcers, such as chronic venous ulcers, and in the treatment of wounds. Ulcers and other wounds may be infected with bacteria which may delay healing. Therefore, eradication of bacteria may increase wound healing. Other wounds which may be treated using an agent identified by a method of the invention include burn wounds, diabetic wounds, eye, lung and urinary tract infections and bacterial infections of intact skin. Any ulcer may be treated with an agent identified by a method of the invention, for example a gastric ulcer. Agents and products of the invention may also be used to prevent sterile wounds from becoming infected with bacteria. Such agents, and products, may also be used for the manufacture of a medicament for use in a method of treating an acute or chronic infection, in the treatment of ulcers or in a method of promoting wound healing. The condition of a patient suffering from an acute or chronic infection or an ulcer or a patient with a wound can be improved by administration of an agent, or product of the invention. A therapeutically effective amount of an agent, or product, of the invention may be given to a host in need thereof. An agent may enhance naturally occurring (endogenous) cationic antimicrobial peptides such as those released by neutrophils. Alternatively, given in combination with an exogenous cationic anti-microbial peptide, the agent may enhance anti-microbial activity of the exogenous peptide.

An agent identified by a method of the invention may be used in combination with a cationic anti-microbial peptide in a method of treatment of the human or animal body by therapy. In particular such combination therapy may be used in the treatment of acute or chronic bacterial infections, in the treatment of ulcers and in the treatment of wounds. An agent and a cationic anti-microbial peptide may also be used for the manufacture of a medicament for use in a method of treating an acute or chronic infection, in the treatment of ulcers or in a method of promoting wound healing. The condition of a patient suffering from an acute or chronic infection or an ulcer or a patient with a wound can be improved by the combined administration of an agent of the invention and a cationic anti-microbial peptide. A therapeutically effective amount of an agent and cationic anti-microbial peptide of the invention and a cationic anti-microbial peptide may be given to a host in need thereof.

Cationic anti-microbial peptides are expressed in neutrophils and at biological boundaries, such as the lung, skin, mucosa and urinary tract. Agents which modulate antimicrobial peptide activity may be used for topical treatment, for example skin or cornea, and for internal use, for example gut, lungs and urinary tract.

An agent identified according to a screening method outlined above or for administration in accordance with the invention may be formulated with standard pharmaceutically acceptable carriers and/or excipients as is routine in the pharmaceutical art, and as fully described in Remmington's Pharmaceutical Sciences, Mack Publishing Company, Eastern Pennsylvania 17$^{th}$ Ed. 1985, the disclosure of which is included herein of its entirety by way of reference. A pharmaceutical composition may comprise an agent of the invention in combination with a cationic anti-microbial peptide and a pharmaceutically acceptable carrier or excipient.

The invention also provides a pharmaceutical composition comprising an inhibitor of a bacterial proteinase/glycosaminoglycan defence pathway, a cationic anti-microbial peptide and a pharmaceutically acceptable carrier or excipient. The agents, compositions and products may be administered by enteral or parenteral routes such as via oral, buccal, anal, pulmonary, intravenous, intra-arterial, intramuscular, intraperitoneal, topical or other appropriate administration routes.

A therapeutically effective amount of an agent, of an agent and a cationic anti-microbial peptide or a product is administered to a patient. The dose of an agent, of an agent and a cationic anti-microbial peptide or a product may be determined according to various parameters, especially according to the substance used; the age, weight and condition of the patient to be treated; the route of administration; and the required regimen. A physician will be able to determine the required route of administration and dosage for any particular patient. A typical daily dose is from about 0.1 to 50 mg per kg of body weight, according to the activity of the specific agent of an agent and a cationic anti-microbial peptide or a product the age, weight and conditions of the subject to be treated, the type and severity of the degeneration and the frequency and route of administration. Preferably, daily dosage levels are from 5 mg to 2 g.

The agent, or inhibitor, and the peptide may be administered simultaneously or sequentially. Preferably the agent, or inhibitor, is administered prior to the administration of the peptide. The agent, or inhibitor, may be administered from 1 minute to 4 hours prior to administration of the peptide, preferably from 5 minutes to 1 hour, from 10 minutes to 30 minutes prior to administration of the peptide. More preferably the agent, or inhibitor, and peptide are administered simultaneously.

The following Examples illustrate the invention.

EXAMPLE 1

The products of $^{35}$S-sulfate labelled fibroblast cultures and the degradation of these products by growth media from bacterial cultures were analysed by 3-12% SDS-polyacrylamide gel electrophoresis (PAGE).

*Pseudomonas aeruginosa* and *Enterococcus faecalis* isolates initially obtained from chronic venous wounds, were grown for 18 hours at 37° C. (stationary phase) in Todd-Hewitt medium. The Streptococcus pyogenes strain AP1 (40/58) was from the World Health Organization Collaborating Centre for References and Research on Streptococci (Prague, Czech Republic) and was grown to stationary phase in C-medium (H. Herwald, M. Collin, W. Muller-Esterl, L. Björck, *J. Exp. Med.* 184, 665 (1996)). Bacteria were pelleted by centrifugation and supernatants were sterile-filtered (0.3 µm). For degradation of radiolabelled proteoglycans, 10 µl of $^{35}$S-sulfate metabolically labelled secreted fibroblast products (A. Schmidtchen, I. Carlstedt, A. Malmström, L.-Å. Fransson, *Biochem. J.* 265, 289 (1990)) were incubated with 10 µl sterile-filtered bacterial supernatants at 37° C. for 6 hours. 10 µ1 TH-medium was included in the control. 10 mM DTT was added for activation of the streptococcal cysteine proteinase.

The connective tissue proteoglycans (PGs) decorin/biglycan and versican constitute the major secreted products of human fibroblasts in vivo as well as in culture (R. V. Iozzo, *Annu. Rev. Biochem.*, 67, 609 (1998)). Analysis by 3-12% SDS-PAGE confirmed previous results identifying decorin (~100 kDa) and versican (~400 kDa) as the dominating extracellular products of $^{35}$S-sulfate labelled fibroblast cultures (A. Schmidtchen, I. Carlstedt, A. Malmström, L.-Å. Fransson, *Biochem. J.* 265, 289 (1990); A. Schmidtchen, L.-Å. Fransson, *Biomed. Chrom.*, 7, 48 (1993)). Addition of growth medium from *P. aeruginosa* and *E. faecalis* cultures resulted in extensive degradation of decorin. Also *S. pyogenes* extracellular products degraded decorin and high molecular weight proteoglycans provided that the reducing agent dithiothreitol (DTT) was added.

The requirement for DTT suggested that the *S. pyogenes* cysteine proteinase was responsible for the degradation. This assumption was confirmed by the effect of a specific cysteine proteinase inhibitor (E64) which completely blocked the effect.

The degraded material was of molecular weight 30-50 kDa, corresponding to the sizes of free/or peptide linked GAG chains as described previously (A. Schmidtchen, L.-Å, Fransson, *Eur. J. Biochem.*, 208, 537 (1992)). Since these experiments did not exclude the possibility of activation of fibroblast matrix metalloproteinases (MMP) by bacterial proteinases (E. H. Burns, A. M. Marciel, J. M. Musser, *Infect. Immun.*, 64, 4744 (1996); T. Okamato et al. *J. Biol. Chem.*, 272, 6059 (1997)), yielding degraded PGs, a series of control experiments were performed with preparations of specific proteinases.

*P. aeruginosa* elastase and alkaline proteinase proteins were prepared by ammonium sulphate precipitation (70% saturation). After dialysis (10 mM Tris, pH 8.0) separation was performed on a High Q anion exchange column (Bio-Rad) using a gradient of 0-1.0 M NaCl in 10 mM Tris, pH 8.0. Elastase was identified in the flow-through fractions whereas alkaline proteinase eluated at ~0.5 M NaCl.

The cysteine proteinase of *S. pyogenes* was purified according to previous protocols (H. Herwald, M. Collin, W. Muller-Esterl, L. Björck, *J. Exp. Med.* 184, 665 (1996)).

The *E. faecalis* strain contained gelatinase and supernatants were used directly. *P. aeruginosa* elastase and alkaline proteinase, the *S. pyogenes* cysteine proteinase and *E. faecalis* gelatinase all degraded purified human cervix decorin as well as $^{35}$S-labelled fibroblast decorin in the conditioned medium. Stepwise ion-exchange chromatography (A.

Schmidtchen, I. Carlstedt, A. Malmströrm, L.-Å. Fransson, *Biochem. J.* 265, 289 (1990)) (for separation of fibroblast-derived MMPs) followed by PBS dialysis of the radiolabelled fibroblast proteoglycans or boiling the fibroblast products to inactivate fibroblast MMPs did not affect degradation. Preincubation (~15 min) of *S. pyogenes* cysteine proteinase with the cysteine proteinase inhibitor E64 abolished degradation.

Another wound pathogen, *Proteus mirabilis* has also been shown to produce extracellular proteinases that release dermatan sulfate.

EXAMPLE 2

We then investigated whether dermatan sulfate (DS), the glycosaminoglycan (GAG) substituent of human decorin (R. V. Iozzo, *Annu. Rev. Biochem.*, 67, 609 (1998)), bound defensin, and whether other sulfated polysaccharides could block the interaction.

The glycosaminoglycans used in these experiments were dermatan sulfate (DS)36, DS13, heparan sulfate (HS)3-6, chondroitin sulfate (CS)-4 and CS-6. The preparation and characterisation of these have been described previously (L. Rodén, J. Baker, J. A. Cifonelli, M. B. Mathews, in *Methods in Enzymology*, V. Ginsburg, ed. (Academic Press, New York, 1973), vol. 28, pp. 73-140; L.-Å. Fransson, I. A. Nieduszynski, C. F. Phelps, J. K. Sheehan, Biochim. Biophys. Acta., 586,179 (1979); L.-Å. Fransson, 1. Sjöberg, B. Havsmark, *Eur. J. Biochem.*, 106, 59 (1980)). Heparin and additional preparations of CS-4 (CS-A from bovine trachea) and 6 (CS-C from shark cartilage) were purchased from Sigma. Dextran sulfate (MW ~500 kDa) was from BDH Biochemical.

Radioiodination of DS36 was performed according to previous protocols (F Cheng, K. Yoshida, D. Heinegard, L. Å. Fransson, *Glycobiology*, 2, 553 (1992)). Slot-binding assays were carried out as follows: α-defensin peptide I (Bachem, Switzerland) was blotted onto nitrocellulose membranes (Hybond, Amersham). Membranes were blocked (PBS, pH 7.4, 0.25% Tween 20, 3% bovine serum albumin) for 1 h and incubated with radiolabelled DS (~20 µl/ml) for 1 h in the same buffer. Unlabelled polysaccharides were added for competition of binding (2 mg/ml). The membranes were washed (3×10 min) (PBS, pH 7.4, 0.25% Tween 20). Bas 2000 radioimaging system (Fuji) was used for visualization of radioactivity.

0.2-5 µg α-defensin 1 was blotted onto nitrocellulose and probed with radioiodinated dermatan sulfate (DS). DS bound to the peptide and binding was inhibited by an excess (~100-fold) of unlabelled DS (DS36; 75% iduronate [IdoA]) as well as by DS13 (>95% IdoA). Chondroitin sulfate (CS)-4 as well as CS-6 did not abolish binding. CS-4 and DS differ mainly in the epimerization of the uronic acid (glucuronate in CS-4 and IdoA in DS) (L.-Å. Fransson, in *The Polysaccharides*, G. O. Aspinall, ed. (Academic Press, New York, 1985), vol 3, pp. 338-406). Among the heparan sulfate (HS) fractions tested (HS 3-6), only those of higher sulfation and IdoA content (HS 5; ~50% IdoA and 62% N-sulfate, HS6; 65% IdoA and 72% N-sulphate) were found to completely displace DS. In addition heparin and dextran sulfate, but not dextran, displaced the radiolabelled DS. Taken together, the results suggest that the GAG-defensin interaction depends on IdoA residues as well as sulfation of the polysaccharide. Since the IdoA in DS and HS/heparin may be 2-O-sulfated (L.-Å. Fransson, in *The Polysaccharides*, G. O. Aspinall, ed. (Academic Press, New York, 1985), vol 3, pp. 338-406), additional modifications of the DS and HS polymers may be required for binding to α-defensin 1.

EXAMPLE 3

To investigate the effects of DS on defensin function, the bactericidal activity of α-defensin 1 against the test organisms *S. pyogenes, E. faecalis* and *P. aeruginosa* was determined.

For anti-microbial assays *S. pyogenes, E. faecalis* and *P. aeruginosa* were grown to mid-log phase in TH-medium. Bacteria were washed and diluted in 10 mM Tris-HCl, pH 7.5, containing 5 mM glucose. 50 µl bacteria ($2\times10^6$ cfu/ml) were incubated with α-defensin at concentrations ranging from 0-40 µg/ml with or without the addition of various GAG chains at concentrations of 2-400 µg/ml. Incubations were carried out at 37° C. for 2 h (*S. pyogenes* and *E. faecalis*) or 4 h (*P. aeruginosa*). To quantitate the microbicidal activity serial dilutions of the incubation mixture were plated on TH agar, incubated at 37° C. over night and the number of CFU were determined.

Figure 1A:
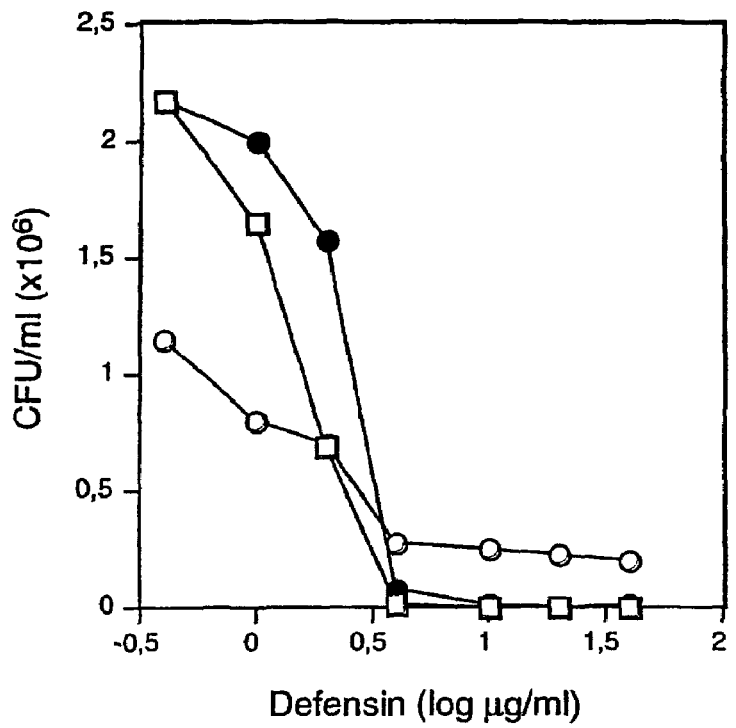
FIG. 1A illustrates the killing of bacteria by α-defensin. $2 \times 10^6$ CFU/ml of *S. pyogenes* (□) *E. faecalis* (●) and *P. aeruginosa* (○) were incubated with α-defensin at the indicated peptide concentrations for 2 h (*S. pyogenes* and *E. faecalis*) or 4 h (*P. aeruginosa*) at 37° C., and CFU were determined.
Figure 1B:
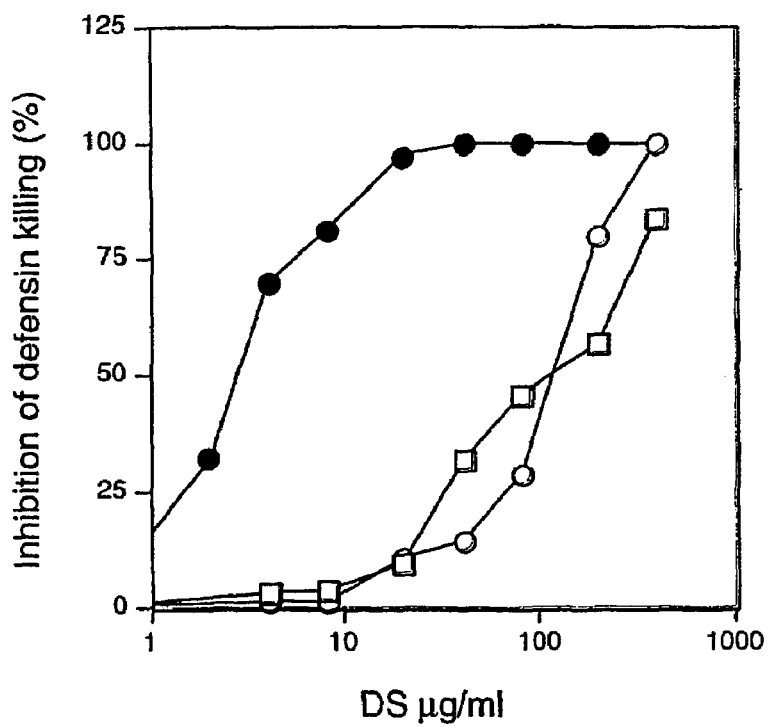
FIG. 1B illustrates the inhibition of defensin-mediated killing of bacteria by dermatan sulfate. The addition of DS at various concentrations (0-400 µg/ml) inhibited the defensin killing of *S. pyogenes* (□) *E. faecalis* (●) and *P. aeruginosa* (○).

The bacterial strains were incubated with 0-40 µg/ml of α-defensin 1. *P. aeruginosa, E. faecalis* and *S. pyogenes* were effectively killed by the defensin at or above concentrations of 4 µg/ml. Addition of DS at concentrations of 20-40 µg/ml (DS/defensin molar ratio ~0.5-1) yielded almost complete reversal of defensin-mediated killing of *E. faecalis* and partial inhibition of killing of the two other species (FIG. 1B). DS at 400 µg/ml (molar ratio ~10:1) almost completely reversed the defensin anti-microbial effects. Since previous experiments showed that DS bound α-defensin 1, and that binding was not inhibited by a ~100-fold excess of HS3 as well as the two CS forms, we addressed the question whether these GAGs were less active in inhibiting defensins. Indeed, when included in the assay (using *S. pyogenes* as the test organism), defensin-mediated bacterial killing was only partly inhibited; HS3, CS4 and CS-6 (Sigma) at 400 µg/ml yielded only 6, 16 and 2% inhibition, respectively.

EXAMPLE 4

To investigate the effects of DS on LL-37 function, the bactericidal activity of LL-37 against the test organisms *S. pyogenes, E. faecalis* and *P. aeruginosa* was determined.

Figure 2:
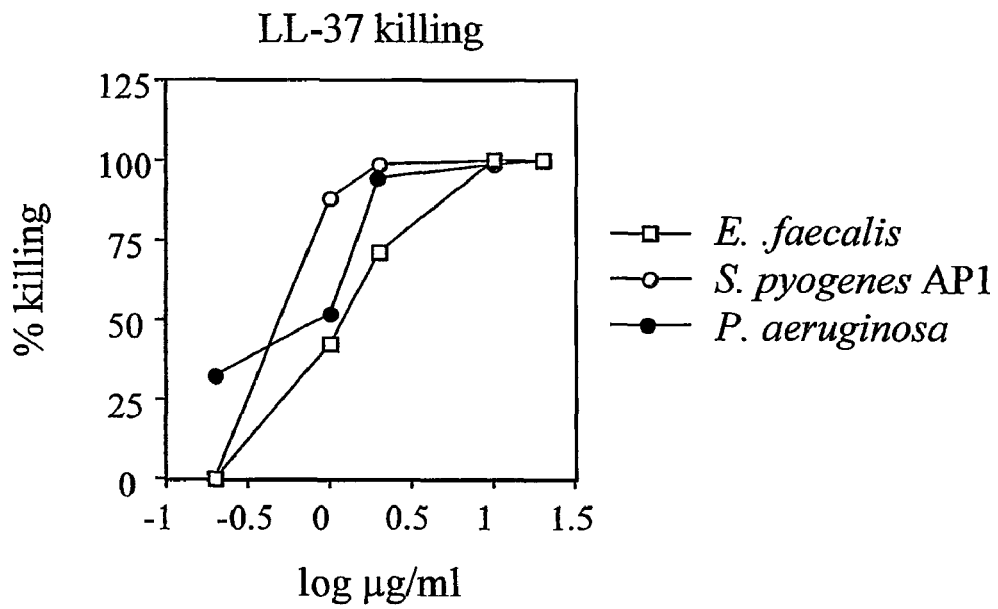
FIG. 2 shows the bactericidal effect of LL-37. $2 \times 10^6$ colony forming units (cfu)/ml of *E. faecalis* (□) *S. pyogenes* AP1 (○), or *P. aeruginosa* (●) were incubated with LL-37 at indicated peptide concentrations for 2 h (*S. pyogenes* and *E. faecalis*) or 4 h (*P. aeruginosa*) at 37° C. in 10 mM Tris-HCl pH 7.5, 5 mM glucose and cfus were determined.
Figure 3:
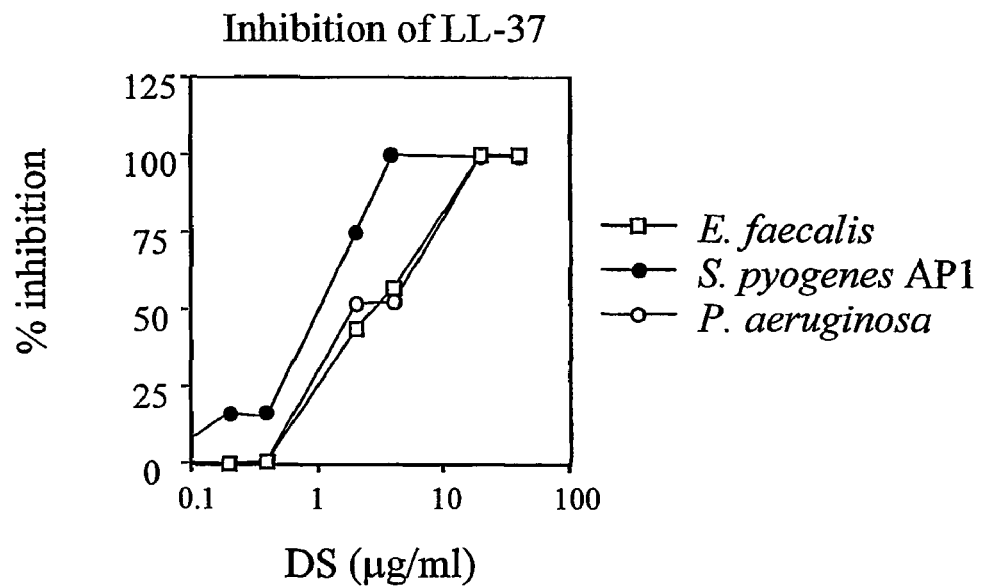
FIG. 3 illustrates the blocking of the bacterial effect of LL-37 by dermatan sulphate (DS). The addition of dermatan sulphate (DS) at various concentrations (0-40 µg/ml) inhibited the LL-37 killing of *E. faecalis* (□), *S. pyogenes* AP1 (●) and *P. aeruginosa* (○). $2 \times 10^6$ cfus/ml of the various bacterial strains were incubated with LL-37 at 10 µg/ml (*E. faecalis* and *P. aeruginosa*) or 2 µg/ml (*S. pyogenes* strain AP1) and dermatan sulphate for 2 h (AP1 and *E. faecalis*) or 4 h (*P. aeruginosa*) at 37° C. in 10 mM Tris-HCl pH 7.5, 5 mM glucose, and cfus were determined.

Anti-microbial assays were carried out as described in Example 3. The results illustrating the antibacterial activity of LL-37 are shown in FIG. 2. The addition of DS at various concentrations (0-40 µg/ml) inhibited the LL-37 killing of *S. pyogenes, E. faecalis* and *P. aeruginosa*. The results are shown in FIG. 3.

EXAMPLE 5

Figure 4:
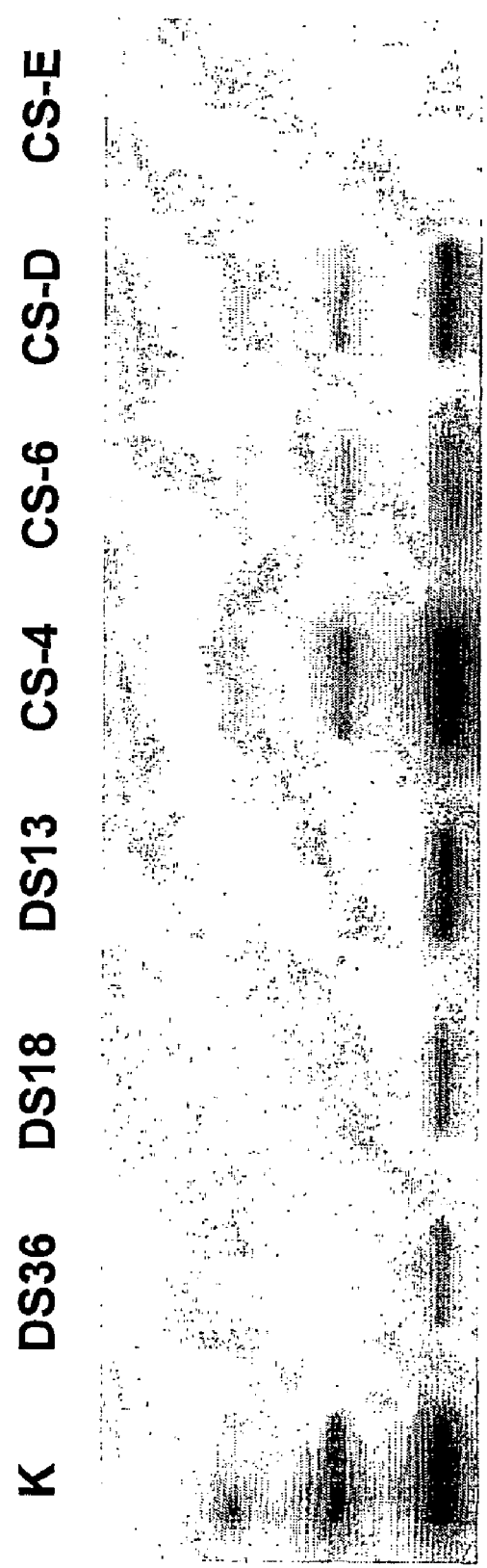
FIG. 4 shows the binding of dermatan sulphate to LL-37. LL-37 (0.2-5 µg) was applied onto nitrocellulose and incubated with iodinated dermatan sulphate (DS36). Different polysaccharides were added for competition of binding. DS36, DS18, DS13 (dermatan sulphate 36, 18, and 13), CS4 and CS6 (chondroitin sulphate 4 and 6), CS-D (chondroitin sulphate D) and CS-E (chondroitin sulphate E).

To investigate whether dematan sulfate (DS) binds LL-37 and whether sulfated polysaccharides could block the interaction, slot-binding assays were carried out as described in Example 2. LL-37 (0.2-5 µg) was applied onto nitrocellulose and incubated with iodinated dermatan sulphate (DS36). Different polysaccharides were added for competition of binding: DS36, DS18, DS13, CS-4, CS-6, CS-D (chondroitin sulphate D) and CS-E (chondroitin sulphate E). The results are shown in FIG. 4. CS-4, CS-6 and CS-D and CS-D did not abolish binding. Radiolabelled DS was, however, displaced by DS-36, DS18, DS13 and CS-E.

EXAMPLE 6

Figure 5:
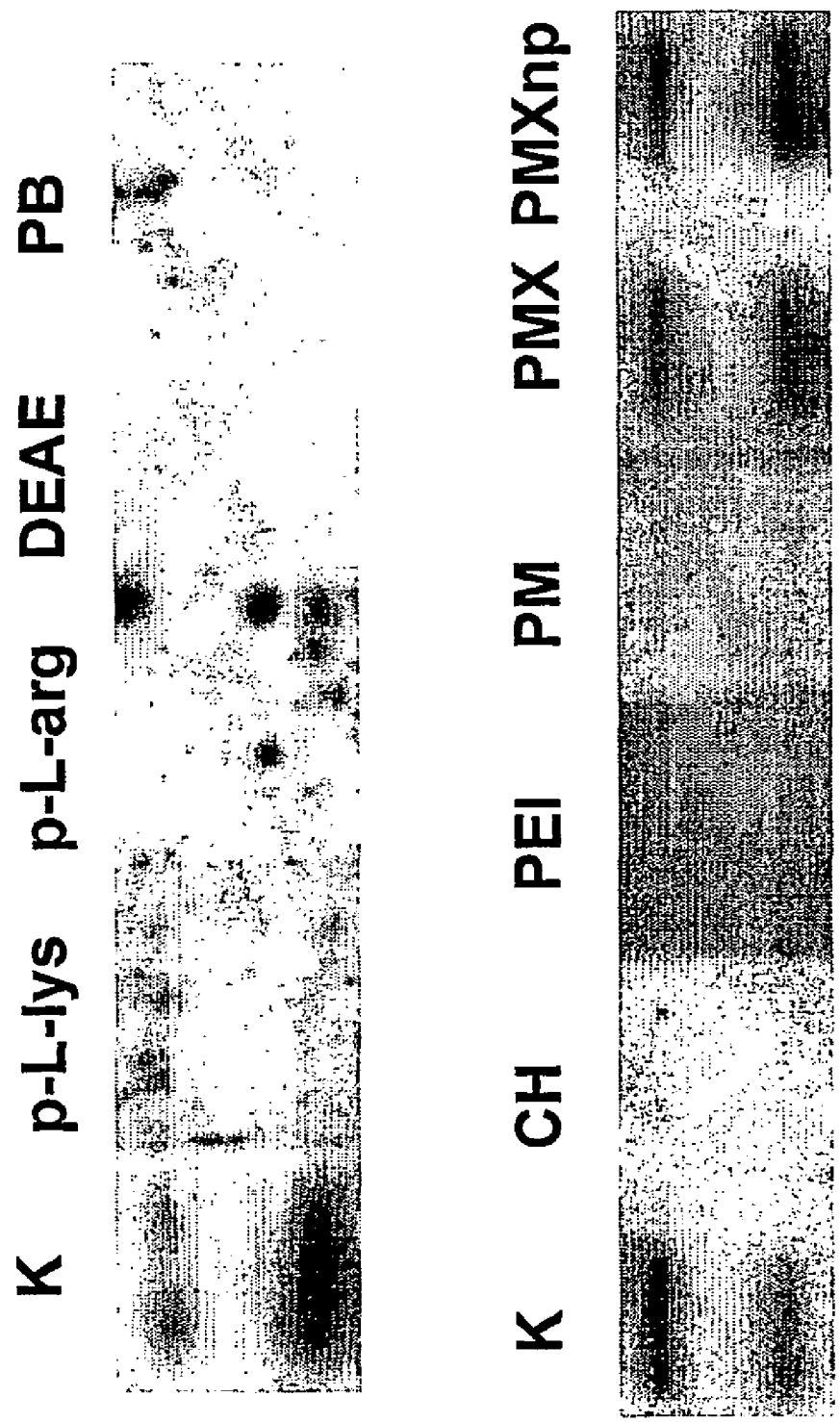
FIG. 5 shows the effects of various cationic molecules on the DS-LL-37 interaction. LL-37 (0.2-5 µg) was applied onto nitrocellulose and incubated with iodinated dermatan sulphate (DS36). Different cationic substances, as indicated on top of the various panels, were added for competition of binding. (a), p-1-lys; poly-L-lysine, p-1-arg; poly-L-arginine, DEAE; DEAE-dextran, PB; polybrene. (b), CH; chitosan, PEI, polyethyleneimine, PM; protamine, PMX; polymyxin B, PMXnp; polymyxin B nonapeptide.

The effects of various cationic molecules on the DS-LL-37 interaction were monitored using slot-blot assays as described in Example 2. The results are shown in FIG. 5. DS binding to LL-37 was blocked by poly-L-lysine, poly-L-arginine, DEAE-dextran, polybrene, chitosan and polyethyleneimine. Reduced levels of binding were observed in the presence of protamine. Polymyxin B and polymyxin B nonapeptide did not block the binding of DS to LL-37.

EXAMPLE 7

To demonstrate that *P. aeruginosa* elastase degrades and inactivates LL-37, 10 μg LL-37 was incubated with 30 mU *P. aeruginosa* elastase in 50 μl 10 mM Tris, pH 7.5 for 0, 1, 5, 15 or 30 minutes or 1, 4 or 20 hours. Equal aliquots of the incubations were analysed on SDS-PAGE (16.5% Tris-Tricine gel) or assayed for bactericidal activity. For the bactericidal assays $2 \times 10^6$ cfus/ml of *E. faecalis* were incubated with 0.1 μg LL-37 for 2 h at 37° C. in 10 mM Tris-HCl pH 7.5, 5 mM glucose. The results shown in FIG. 6 show that LL-37 is degraded and inactivated by *P. aeruginosa* elastase.

The LL-37 degradation products were analysed by liquid chromatography mass spectrometry (LC-MS) followed by time of flight (TOF) MS-MS. Major peptide fragments yielding fragment masses of 3708.859, 3178.637, 2822.450, 2326.269 and 1401.748 were detected and further analysed. The cleavage points and the proposed antibacterial region of LL-37 are shown in FIG. 7.

The degradation of LL-37 by 3 mU *E. faecalis* gelatinase or 3 mU *S. pyogenes* cysteine proteinase was monitored by incubating 1 μg LL-37 for 1 hour and 6 hours. The degradation products were analysed by SDS-PAGE on 16.5% Tris-Tricine gels and compared to the degradation products following incubation of 6 mU *P. aeruginosa* elastase with 1 μg LL-37 for 5 minutes and 1 hour. The results are shown in FIG. 8.

EXAMPLE 8

The effects of various substances on the degradation of LL-37 were determined by incubating 1 μg LL-37 with 12 mU *P. aeruginosa* elastase, 6 mU *E. faecalis* gelatinase or 6 mU, *S. pyogenes* proteinase for 1 hour in the presence and absence of inhibitors. The resulting material was analysed by SDS-PAGE (16.5% Tris-Tricine gels). Degradation was abolished by the metalloproteinase inhibitors GM6001 (100 μM) and 1,10-phenantroline (2 mM) which both inhibited *P. aeruginosa* elastase and *E. faecalis* gelatinase or by the inhibitor E64 (10 μM) which inhibited *S. pyogenes* cysteine proteinase (FIG. 9).

DS36 and CS-E, and to a lesser extent CS-A and CS-C, inhibited the degradation of LL-37 by *P. aeruginosa* elastase (FIG. 10). Sulfated disaccharides of the structure [ΔUA(2S)-GalNAc(4,6S)] (FIG. 11) and sucroseoctasulphate (FIG. 12) also inhibited the degradation of LL-37 by *P. aeruginosa* elastase.

---

The invention claimed is:

1. A method to identify an agent that inhibits the binding interaction between a glycosaminoglycan released by a bacterial extracellular proteinase and a cellular cationic anti-microbial peptide comprising the steps of: (i) providing a glycosaminoglycan released by a bacterial extracellular proteinase as a first component; (ii) providing a cellular cationic anti-microbial peptide as a second component; (iii) contacting the first and second components with a test agent wherein said first and second components would interact under the same conditions in the absence of said test agent, and (iv) monitoring any binding interaction between the first and second components thereby determining whether said test agent inhibits the binding interaction between the first and second components.

2. The method according to claim 1, wherein the cationic anti-microbial peptide is a defensin.

3. The method according to claim 2, wherein the defensin is an alpha-defensin.

4. The method according to claim 1, wherein the cationic anti-microbial peptide is LL-37.

5. The method according to claim 1, wherein the glycosaminoglycan has a high iduronate content.

6. The method according to claim 1, wherein said glycosaminoglycan has a high degree of sulfation.

7. The method according to claim 1, wherein said glycosaminoglycan is dermatan sulfate.

\* \* \* \* \*

SEQUENCE LISTING

```
<160> NUMBER OF SEQ ID NOS: 2

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
 1               5                  10                  15

Phe Lys Arg Ile Val Gln Arg Ile Lys Asp Phe Leu Arg Asn Leu Val
             20                  25                  30

Pro Arg Thr Glu Ser
         35

<210> SEQ ID NO 2
<211> LENGTH: 30
<212> TYPE: PRT
<213> ORGANISM: Homo sapiens

<400> SEQUENCE: 2

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
             20                  25                  30
```